US00PP29548P2

(12) United States Plant Patent
Hansen

(10) Patent No.: US PP29,548 P2
(45) Date of Patent: Jul. 24, 2018

(54) ***MONARDA* PLANT NAMED 'PINK FROSTING'**

(50) Latin Name: ***Monarda* hybrid**
Varietal Denomination: Pink Frosting

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 35 days.

(21) Appl. No.: 15/530,505

(22) Filed: Jan. 23, 2017

(51) Int. Cl.
*A01H 5/02* (2018.01)

(52) U.S. Cl.
USPC ..... Plt./455

(58) Field of Classification Search
USPC ..... Plt./263.1, 455
See application file for complete search history.

(56) References Cited

PUBLICATIONS

Walters Garden's 2016-2017 Catalogue. https://www.provenwinners.com/sites/provenwinners.com/files/catalogs_pdfs/1-26_front_pages.pdf. 5 pages.*

* cited by examiner

*Primary Examiner* — Susan McCormick Ewoldt
*Assistant Examiner* — Karen M Redden

(57) ABSTRACT

The new and distinct cultivar of ornamental cultivar of bee balm plant named *Monarda* 'Pink Frosting' has rounded, compact, clumping habit with short rhizomes, basally branching stems, medium to dark green foliage, numerous large pastel pink-colored flowers creating excellent flower coverage and foliar resistance to powdery mildew. The new plant is useful for landscaping in containers or in the ground, as accent plants or en masse.

1 Drawing Sheet

Botanical classification: *Monarda* hybrid.
Variety denomination: 'Pink Frosting'.

BACKGROUND OF THE INVENTION

The present invention relates to the new and distinct cultivar of bee balm plant, botanically known as *Monarda* 'Pink Frosting', and hereinafter also referred to solely by the cultivar name 'Pink Frosting' or the "new plant". The new plant was selected from seed collected by the hybridizers on Oct. 7, 2009 from an open pollination of *Monarda* 'Petite Delight' U.S. Plant Pat. No. 10,784 at the hybridizing plot of a wholesale perennial nursery in Zeeland, Mich., USA. The male plant was unknown, but may have been any one of several in the breeding field as these plants are frequently insect pollinated. The plant was a single selection initially made in the summer of 2011 from the batch of seeds sown in the fall of 2009. Further selection was completed in the trial beds of the same nursery in Zeeland, Mich. in the summer of 2013 and the plant was assigned the breeder code of H9-42-52. The plant has been asexually propagated by shoot tip cuttings since in 2013 at the same nursery in the greenhouses in Zeeland, Mich., and the subsequent asexually propagated plants have been found to be stable, true to type and identical to the original selection.

No plants of *Monarda* 'Pink Frosting' have been sold in this country, or anywhere in the world, under this or any name, prior to the filing of this application, nor has any disclosure of the new plant been made prior to the filing of this application with the exception of that which was sold or disclosed within one year of the filing of this application and was either derived directly or indirectly from the inventors.

BRIEF SUMMARY OF THE PLANT

*Monarda* 'Pink Frosting' is unique from its parent and all other bee balm plants known to the inventors. The nearest comparison varieties known to the inventor are 'Pardon My Pink' U.S. Plant Pat. No. 24,244, 'Bubblegum Blast' U.S. Plant Pat. No. 27,497, 'Pink Lace' U.S. Plant Pat. No. 18,367, 'Pink Supreme' U.S. Plant Pat. No. 14,204, 'Sugar Lace' U.S. Plant Pat. No. 22,918 and the female parent 'Petite Delight'. Compared with 'Petite Delight', the new plant is slightly taller, denser in habit and the flower color is different. 'Bubblegum Blast' differs from the new plant in being taller and the flower color is different. Compared with 'Pardon My Pink', the new plant is taller and broader and the flower color is pastel pink compared with the fuchsia purple. 'Pink Lace' differs from the new plant in being shorter in habit and the flower color is deep pink rather than pastel pink. Both 'Pink Supreme' and 'Sugar Lace' are taller in habit and the flowers of 'Pink Supreme' are brighter pink while those of 'Sugar Lace' have a deeper and more purple hue than the new plant.

The following are traits of *Monarda* 'Pink Frosting' that in combination distinguish it from all other bee balm known to the inventor:

1. Winter-hardy, clumping habit with short compact rhizomes;
2. Medium to dark-green lanceolate leaves;
3. Powdery mildew resistant foliage;
4. Large-sized, pastel pink-colored flowers that completely cover the foliage.
5. Long flowering period beginning mid-summer.

BRIEF DESCRIPTION OF THE DRAWINGS

The photographs of the new plant demonstrate the unique traits of 'Pink Frosting' and the overall appearance of the plant at two-years-old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
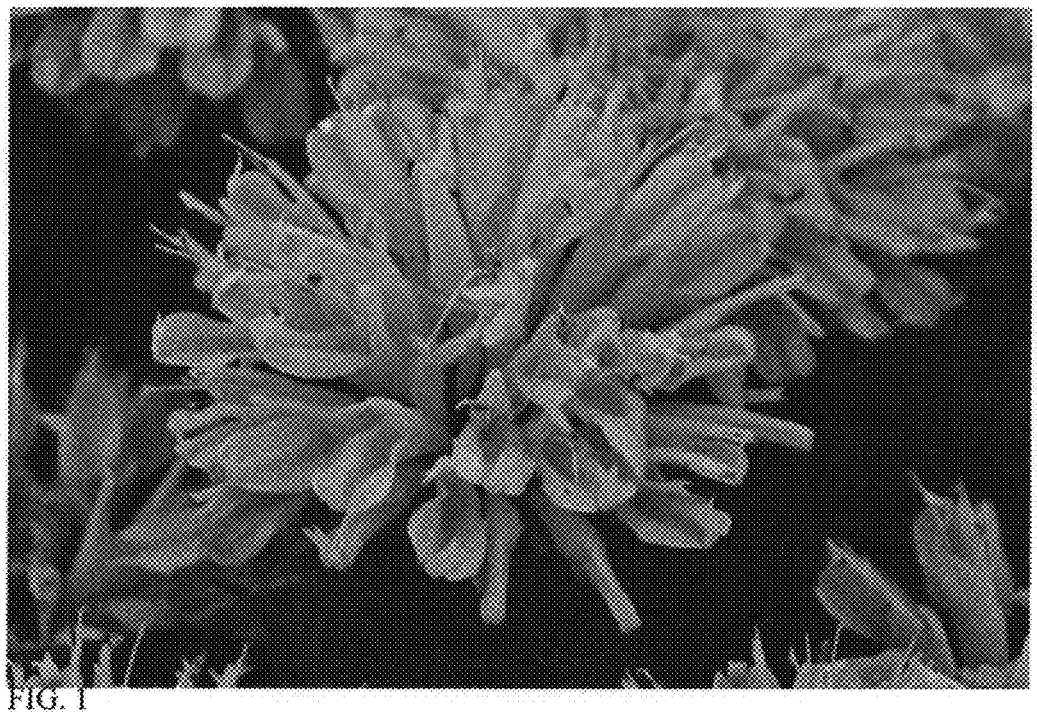
FIG. 1 shows a close-up of the flowers.
Figure 2:
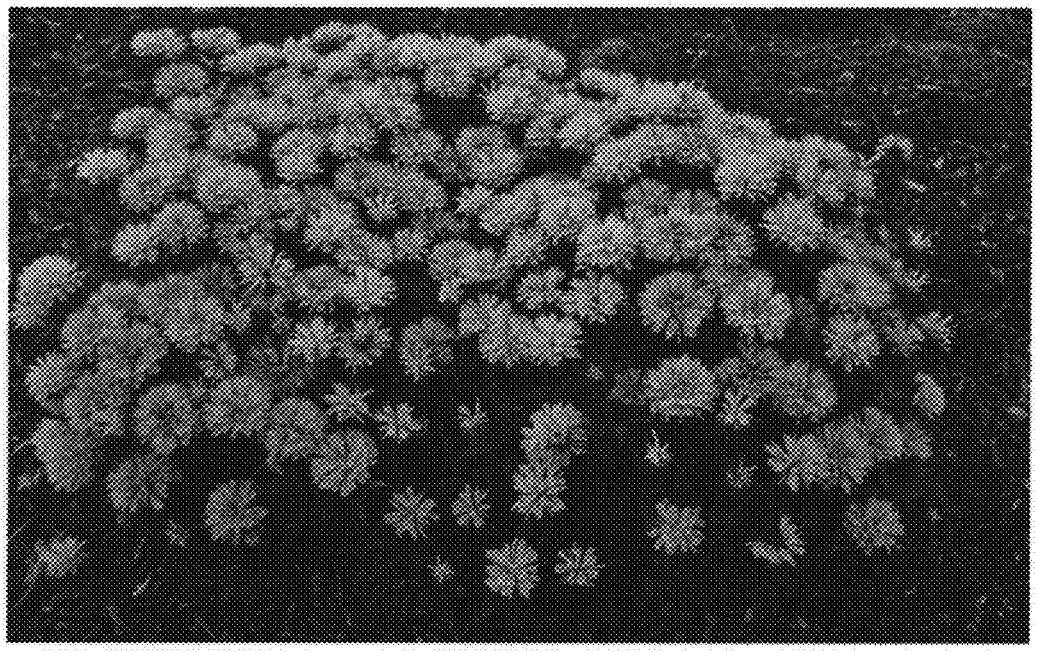
FIG. 2 shows the new plant in flower in the landscape.

The following descriptions and color references are based on the 2001 edition of The Royal Horticultural Society Colour Chart except where common dictionary terms are used. *Monarda* 'Pink Frosting' has not been observed under all possible environments. The phenotype may vary slightly with different growing environments such as temperature, light, fertility, soil pH, moisture and maturity levels, but without any change in the genotype. The following observations and size descriptions are based on two-year-old plants in full-sun trial gardens at a nursery in Zeeland, Mich. with supplemental fertilizer and water as needed but without plant growth regulators or pinching.

Botanical classification: *Monarda* hybrid;

Parentage: Female (seed) parent is 'Petite Delight'; male (pollen) parent is unknown;

Plant habit: Winter-hardy herbaceous perennial, compact, rounded dome, producing 18 to 30 stems spreading by short compact rhizomes; to about 45 cm tall at flowering and about 60 cm wide at flower height; flowering begins mid-summer in Michigan and continuing for about 5 to 6 weeks;

Propagation: Stem cuttings;

Time to produce finished crop in 3.8 liter pots: About 10 to 12 weeks; moderate rate of growth;

Root: Fine, fibrous and freely branching; color creamy white to tan depending on soil type;

Leaves: Simple, lanceolate, opposite, serrated, puberulent to pubescent above and below; lustrous above, matte below; acute apex, rounded to cuneate base; to about 7.8 cm long by about 3.2 cm wide, average about 6.5 cm long and 2.7 cm wide;

Leaf color: Young expanding leaves nearest RHS 145C on adaxial surface and on abaxial surface nearest RHS 145C; mature adaxial leaves nearest RHS 139A and abaxial surface nearest RHS 137C;

Foliage fragrance: Pleasantly suaveolent, lemony;

Veins: Pinnate; pubescent abaxial with minute puberulent to glabrous adaxial; slightly sunken above and costate below;

Vein color: Young expanding abaxial leaves nearest RHS 157A, adaxial nearest RHS 145C; mature abaxial vein nearest RHS 145C and adaxial nearest RHS 160D with some distal adaxial veins becoming tinted with nearest RHS N186C;

Bracts: Between distal leaves and flowers; sessile; deltoid to lanceolate, with acuminate apex and truncate base; about seven per terminal verticillaster; average about 1.8 cm long and 1.3 cm wide;

Bract color: Abaxial and adaxial nearest RHS 139B with slight tinting of nearest RHS N186C and some most-distal adaxial bract veins becoming completely RHS N186C;

Petiole: Pubescent abaxial and adaxial, concavo-convex; to about 4.0 mm long and 2.5 mm wide at base; average about 3.0 mm long and 2.0 mm wide;

Petiole color: Abaxial nearest RHS 145C, adaxial nearest RHS 137D along margins with light to light tinting of nearest RHS N187A in center;

Stems: Quadrangular, sparsely pubescent; about 3.5 mm across at base and about 26.0 to 30.0 cm long;

Stem color: Nearest RHS 146D toward base with strong tinting of nearest RHS N187A in distal regions of heavy light exposure;

Lower branches: Quadrangular, puberulent, pubescent; attitude upright; average about four per main stem; about 2.0 mm across at base and up to 25 cm long;

Lower branch color: Same as main stem;

Nodes: About 16 per main stem and 8 on lowest branches; average internode about 2.5 cm, shorter in lower portion; color nearest RHS 145C;

Flowers: Single, bilabiate, actinomorphic; arranged in terminal verticillate head about 9.2 cm across and 4.0 cm tall opening from the center and progressing outwardly and down; each flower persisting about 5 days in Michigan; numerous, about 90 flowers per head; inflorescence attitude upright, individual flowers outwardly toward outer portion of verticil to slightly upright in center of verticil; self-cleaning;

Flower period: Usually late June into August; about four to five weeks;

Flower fragrance: Moderately spicy and sweet;

Buds one to two days prior to opening: Narrowly oblanceolate; terete; arcuate downward; rounded apex; about 2.2 cm long and about 3.5 mm tall and 2.0 mm across in the middle;

Bud color one to two days prior to opening: Nearest RHS 72A;

Petals: Bilabiate, arcuate downward; fused into tube in basal 1.9 cm, nearly straight, involute in middle portion, apex acute, pubescent abaxial and glabrous adaxial; lower lip with three apical lobes; furrowed in longitudinal center; two side lobes rounded apex; distal petals glabrous adaxial and pubescent abaxial; fused tube portion pubescent abaxial and adaxial from base to rictus; upper lip about 2.9 cm long and about 3.0 mm wide at fusion, lower lip about 2.5 cm long; lower lip 6.5 mm across midway between fusion and apex, center lobe emarginate 1.0 mm deep, 4.0 mm long and 2.0 mm across, about 1.0 mm long and 2.2 mm across;

Petal color: Lower lip adaxial center between RHS 72C and RHS 72B, distal margin lighter than RHS 75B, lobe between RHS 75B and RHS 75C; lower lip abaxial color nearest RHS 72C; upper lip adaxial nearest RHS 72C, upper lip abaxial between RHS 72C and RHS 72D; fused tube abaxial base between white, lighter than RHS 155D and RHS N155B;

Androecium: Two;

*Filaments*.—Adnate to adaxial petal about 13.5 mm from base; about 14.0 mm long and 0.5 mm diameter; color distally between RHS 65D and RHS N155B, proximally white, lighter than RHS 155D.

*Anther*.—Two, typically laterally connate; oblong elliptic, dorsifixed, longitudinal; 1.7 mm by 0.5 mm; color nearest RHS 187A.

*Pollen*.—Abundant, elliptic to globose, less than 0.1 mm; color nearest RHS 155D.

Gynoecium: One per flower;

*Style*.—About 2.5 cm by 0.5 mm; color nearest RHS N155B toward distal end, lightening to lighter than RHS 155D toward base.

*Stigma*.—Bifurcated in the distal 1.5 mm, 0.25 mm in diameter; color nearest RHS 75A.

*Ovary*.—1.0 mm by 0.75 mm; color between RHS 143D and RHS 144B.

Sepals: Five, narrowly acute to apiculate apex, base fused in basal 8.5 mm forming calyx about 9.5 mm long and 1.2 mm diameter; apex glandular and with minute hairs on abaxial surface;

Sepal color: Abaxial nearest RHS 145B with light tinting of nearest RHS N187A toward apex and veins of nearest RHS 146B; adaxial nearest RHS 145C with veins of nearest RHS 146B and apex of nearest RHS N187A;

Pedicel: Terete; glabrous, about 1.0 mm long and 0.7 mm diameter; color nearest RHS 145B;

Peduncle: Pubescent, stiff, strong, erect, quadrangular to about 3.5 mm across at base and average about 42.0 cm long;

Peduncle color: Nearest RHS 146D with light tinting of nearest RHS 176B in areas of heavy light exposure;

Fruit: Single nutlet, slightly flattened ovoid, about 1.2 mm long and 1.0 mm wide; color nearest RHS 202A;

Hardiness: The new plant grows best with plenty of moisture and adequate drainage; hardy to at least from USDA zone 4 through 9;

Disease and pest resistance: Demonstrated powdery mildew resistance (*Sphaerotheca pannosa* var. *rosa*);

It is claimed:

1. A new and distinct cultivar of ornamental bee balm plant, *Monarda* 'Pink Frosting', as herein described and illustrated.

* * * * *